US006258809B1

(12) United States Patent
Rajagopalan et al.

(10) Patent No.: US 6,258,809 B1
(45) Date of Patent: Jul. 10, 2001

(54) 6-ARYLOXY AND ARYLTHIOPURINES

(75) Inventors: Parthasarathi Rajagopalan, Wilmington, DE (US); Robert John Chorvat, West Chester, PA (US); Rajagopal Bakthavatchalam, Wilmington, DE (US); James Peter Beck, Newark, DE (US); Paul Joseph Gilligan; Richard Eric Olson, both of Wilmington, DE (US)

(73) Assignee: DuPont Pharmaceuticals Company, Wilmington, DE (US)

( * ) Notice: Subject to any disclaimer, the term of this patent is extended or adjusted under 35 U.S.C. 154(b) by 0 days.

(21) Appl. No.: 09/518,354

(22) Filed: Mar. 3, 2000

Related U.S. Application Data

(62) Division of application No. 08/822,257, filed on Mar. 20, 1997.
(60) Provisional application No. 60/014,090, filed on Mar. 26, 1996.

(51) Int. Cl.[7] .................... C07D 473/02; C07D 473/30; C07D 473/38; A61K 31/522; A61P 25/24

(52) U.S. Cl. ...................... 514/228.5; 514/234.5; 514/241; 514/261; 514/262; 514/263; 514/265; 514/266; 544/61; 544/118; 544/212; 544/266; 544/267; 544/268; 544/269; 544/270; 544/271; 544/273; 544/276

(58) Field of Search ................ 514/228.5, 234.5, 514/262, 263, 265, 266, 261, 241; 544/61, 118, 212, 266, 269, 272, 273, 267, 268, 271, 276

(56) References Cited

U.S. PATENT DOCUMENTS

| | | | |
|---|---|---|---|
| 2,746,961 | * 5/1956 | Hitchings et al. | 260/252 |
| 4,076,711 | 2/1978 | Ganguly et al. | 260/256.4 |
| 4,801,710 | * 1/1989 | Maccoss et al. | 544/244 |
| 4,916,224 | 4/1990 | Vince et al. | 544/254 |
| 5,153,318 | * 10/1992 | Rideout | 536/24 |
| 5,753,635 | * 5/1998 | Buckman et al. | 514/81 |

FOREIGN PATENT DOCUMENTS

| | | |
|---|---|---|
| 100951 | * 10/1973 | (DE) . |
| 0298467 | 1/1989 | (EP) . |
| 664294 A1 | * 7/1995 | (EP) . |
| 920267 | * 3/1963 | (GB) . |
| 56-131587 | 10/1981 | (JP) . |
| 59-062595 | 4/1984 | (JP) . |
| 59-62595 | 4/1984 | (JP) . |
| 60-194443 | 10/1985 | (JP) . |
| 3-44630 | * 2/1991 | (JP) . |
| 9411050 | 5/1994 | (WO) . |
| 9533727 | 12/1995 | (WO) . |
| 9533750 | 12/1995 | (WO) . |
| 9534563 | 12/1995 | (WO) . |

OTHER PUBLICATIONS

Elion et al, J. Amer. Chem. Soc., 81, 1959, 1898–1902.*
Johnston, T.P. et al, J. Amer. Chem. Soc., 80, 1958, 6265–71.*
Ukena, D. FEBS Lett. 1987, 215(2), 203–8.*
Harnden et al, J. Med. Chem. 1989, 32(8), 1738–43.*
El–Bardan et al, J. Indian Chem. Soc. 1997, 74(7), 575–578.*
Keck et al, J. Org. Chem. 1978, 43(13), 2587–90.*
Kaiwar et al, J. Chem. Soc., Perkin Trans. 1 1995, (18), 2281–7.*
Rivier et al., *Proc. Nat'l. Acad. Sci.*, vol. 80, p. 4851 (1983).
W. Vale et al., *Science*, vol. 213, p 1394 (1981).
W. Vale et al., *Recent Progress in Hormone Research*, vol. 39, p 245 (1983).
G.F. Koob, *Persp. Behav. Med.*, vol. 2, p 39 (1985).
E.B. DeSouza et al.,*Journal Of Neuroscience*, vol. 5, p 3189 (1985).
J.E. Blalock, *Physiological Reviews*, vol. 69, p 1 (1989).
J.E. Morley, *Life Science*, vol. 41, p 527, (1987).
E.B. DeSouza, *Hospital Practice*, vol. 23, p 59, (1988).
C.B. Nemeroff et al., *Science*, vol. 226, p 1342 (1984).
C.M. Banki et al., *American Journal of Psychiatry*, vol. 144, p 873 (1987).
R.D. France et al., *Biol. Psychiatry*, vol. 23, p 86 (1988).
M. Arato et al., *Biol. Psychiatry*, vol. 25, p 355 (1989).
C.B. Nemeroff et al., *Arch. Gen. Psychiatry*, vol. 45, p 577 (1988).
P.W. Gold et al., *American Journal Of Psychiatry*, vol. 141, p 619 (1984).
F. Holsboer et al., *Psychoneuroendocrinology*, vol. 9, p 147 (1984).

(List continued on next page.)

*Primary Examiner*—John M. Ford
*Assistant Examiner*—Thomas McKenzie
(74) *Attorney, Agent, or Firm*—Kenneth B. Rubin; Kalim S. Fuzail

(57) ABSTRACT

Novel compounds and pharmaceutical compositions thereof, and methods of using same in treating anxiety, depression, and other psychiatric and neurological disorders. The novel compounds provided by this invention are those of the following formulae:

I                          II wherein $R^1$, $R^{13}$, X, Y, Z, G and Q are as defined herein.

5 Claims, No Drawings

OTHER PUBLICATIONS

P.W. Gold et al., *New England Journal Of Medicine*, vol. 314, p 1129 (1986).

R.M. Sapolsky, *Arch. Gen. Psychiatry*, vol. 46, p 1047 (1989).

Grigoriadis et al., *Neuropsychopharmacology*, vol. 2, p 53 (1989).

D.R. Britton et al., *Life Science*, vol. 31, p 363 (1982).

C.W. Berridge and A.J. Dunn, *Regul. Peptides*, vol. 16, p 83 (1986).

C.W. Berridge and A.J. Dunn, *Horm. Behav.*, vol. 21, p 393 (1987).

C.W. Berridge and A.J. Dunn, *Brain Research Reviews*, vol. 15, p 71 (1990).

K.T. Britton et al., *Psychopharmacology*, vol. 86, p 170 (1985).

K.T. Britton et al., *Psychopharmacology*, vol. 94, p 306 (1988).

N.R. Swerdlow et al., *Psychopharmacology*, vol. 88, p 147 (1986).

G.F. Koob and K.T. Britton, *Corticotropin–Releasing Factor: Basic and Clinical Studies Of A Neuropeptide*, p 221 (1990).

Tanji et al., *Chem. Pharm. Bull.*, vol. 39, p 3037–3040 (1991).

Settimo et al., *Il Farmaco*, Ed. Sc., vol. 35, p 308–323 (1980).

Biagi et al., *Il Farmaco*, vol. 49, p 183–186 (1994).

Thompson et al., *J. Med. Chem.*, vol. 34, p 2877–2882 (1991).

Kelley et al., *J. Med. Chem.*, vol. 31, p 606–612 (1990).

Kelley et al., *J. Med. Chem.*, vol. 33, p 1360–1363 (1990).

Kelley et al., *J. Heterocyclic Chem.*, vol. 28, p 1099 (1991).

Khairy et al., *J. Heterocyclic Chem.*, vol. 22, p 853 (1985).

*Remington's Pharmaceutical Sciences*, 17th ed., Mack Publishing Co., Easton, PA, p 1418 (1985).

P.J. Munson and D. Rodbard, *Anal. Biochem.*, vol. 107, p 220 (1980).

G. Battaglia et al., *Synapse*, vol. 1, p 572 (1987).

Kaiwar et al., *J. Chem. Soc.*, Perkin Trans. 1, p 2281–2287 (1995).

Kohda et al., *Biological Pharm. Bull.*, vol. 18, No. 3, p 424–430 (1995).

Buck et al., *Tetrahedron*, vol. 50, No. 30, p 9195–9206 (1994).

Chae et al., *J. Med. Chem.*, vol. 37, p 342–347 (1994).

Krenitsky et al., *J. Med. Chem.*, vol. 32, p 1471–1475, (1989).

Ronsisvalle et al., *Il Farmaco*, vol. 44, No. 4, p 383–390 (1989).

Harnden et al., *J. Med. Chem.*, vol. 32, p 1738–1743, (1989).

Ukena et al., *FEBS Letters*, vol. 215, No. 2, p 203–208 (May 1987).

Drawbaugh et al., *J. Med. Chem.*, vol. 19, No. 11, p 1342–1345 (1976).

Israel et al., *J. Het. Chem.*, vol. 8, No. 6, p 1019–1023 (1971).

*Chem. Abstr.*, vol. 123, No. 25, Dec. 18, 1995, p 1249, col. 2, the Abstract No. 340767a, Reese C., EP664,294, Jan. 19, 1994.

*Chem. Abstr.*, vol. 120, No. 21, May 23, 1994, p 398, col. 1, the abstract No. 263837g, Shibata, T., JP 9401793, Jun. 18, 1992.

*Chem. Abstr.*, vol. 117, No. 1, Jul. 6, 1992, p 799, col. 1, the abstract No. 7889q, El–Bayouki, K.A.M., An. Quim. 1991, 87(7), 899–902.

*Chem. Abstr.*, vol. 111, No. 9, Aug. 28, 1989, p 736, the abstract No. 77826, Bois–Choussy, M., Eur. J. Med. Chem. 1988, 23(6), 539–46 (Fr).

*Chem. Abstr.*, vol. 101, No. 9, Aug. 27, 1984, p 647, col. 2, the abstract No. 72754a, S.S. Pharmaceutical Co., JP 84 62,595, Apr. 10, 1984.

*Chem. Abstr.*, vol. 96, No. 15, Apr. 12, 1982, p 705, col. 1, the abstract No. 122819b, S.S. Pharmaceutical Co., JP 81,131,587, Oct. 15, 1981.

*Chem. Abstr.*, vol. 96, No. 9, Mar. 1, 1982, p 616, col. 2, the abstract No. 69024k, S.S. Pharmaceutical Co., JP 81,131,586, Oct. 15, 1981.

*Chem. Abstr.*, vol. 89, No. 13, Sep. 25, 1978, p 357–358, col. 2, the Abstract No. 102934n, Breter, H., Biocheim. Biophys. Acta, 1978, 518(2), 205–15 (Eng).

*Chem. Abstr.*, vol. 87, No. 3, Jul. 18, 1977, p 639, col. 7, the abstract No. 23126f, Arya, V.P., Indian J. Chem., Sect B 1976, 14B (10), 756–8 (Eng).

*Chem. Abstr.*, vol. 77, No. 19, Nov. 6, 1972, p 6, col. 2, the abstract No. 121989c, Niebch, G., Z. Naturforsch. B 1972, 27(6), 685–82 (Ger).

Chalmers et al., *TiPS*, vol. 17, p 166–172.

Higashino et al., *Heterocycles*, vol. 15(1), p 483–7 (1981).

Higashino et al., *Fukusokan Kagaku Toronkai Koen Yoshishu*, 12th, p 171–5 (1979).

Higashino et al., *Chem. Pharm. Bull.*, vol. 28(1), p 337–43 (1980).

Higashino et al., *Yakugaku Zasshi*, vol. 99(10), p 1031–6 (1979).

Stratakis et al., Chapter 13 (1997).

\* cited by examiner

6-ARYLOXY AND ARYLTHIOPURINES

This application is a division of U.S. Ser. No. 08/822,257, filed Mar. 20, 1997 which claims benefit of U.S. Provisional Application No. 60/014,090, filed Mar. 26, 1996.

FIELD OF THE INVENTION

This invention relates to novel compounds and pharmaceutical compositions, and to methods of using same in the treatment of psychiatric disorders and neurological diseases including major depression, anxiety-related disorders, post-traumatic stress disorder, supranuclear palsy and feeding disorders.

BACKGROUND OF THE INVENTION

Corticotropin releasing factor (herein referred to as CRF), a 41 amino acid peptide, is the primary physiological regulator of proopiomelanocortin(POMC) -derived peptide secretion from the anterior pituitary gland [J. Rivier et al., *Proc. Nat. Acad. Sci. (USA)* 80:4851 (1983); W. Vale et al., *Science* 213:1394 (1981)]. In addition to its endocrine role at the pituitary gland, immunohistochemical localization of CRF has demonstrated that the hormone has a broad extra-hypothalamic distribution in the central nervous system and produces a wide spectrum of autonomic, electrophysiological and behavioral effects consistent with a neurotransmitter or neuromodulator role in brain [W. Vale et al., *Rec. Prog. Horm. Res.* 39:245 (1983); G. F. Koob, *Persp. Behav. Med.* 2:39 (1985); E. B. De Souza et al., *J. Neurosci.* 5:3189 (1985)]. There is also evidence that CRF plays a significant role in integrating the response of the immune system to physiological, psychological, and immunological stressors [J. E. Blalock, *Physiological Review* 69:1 (1989); J. E. Morley, *Life Sci.* 41:527 (1987)].

Clinical data provide evidence that CRF has a role in psychiatric disorders and neurological diseases including depression, anxiety-related disorders and feeding disorders. A role for CRF has also been postulated in the etiology and pathophysiology of Alzheimer's disease, Parkinson's disease, Huntington's disease, progressive supranuclear palsy and amyotrophic lateral sclerosis as they relate to the dysfunction of CRF neurons in the central nervous system [for review see E. B. De Souza, *Hosp. Practice* 23:59 (1988)].

In affective disorder, or major depression, the concentration of CRF is significantly increased in the cerebral spinal fluid (CSF) of drug-free individuals [C. B. Nemeroff et al., *Science* 226:1342 (1984); C. M. Banki et al., *Am. J. Psychiatry* 144:873 (1987); R. D. France et al., *Biol. Psychiatry* 28:86 (1988); M. Arato et al., *Biol Psychiatry* 25:355 (1989)]. Furthermore, the density of CRF receptors is significantly decreased in the frontal cortex of suicide victims, consistent with a hypersecretion of CRF [C. B. Nemeroff et al., *Arch. Gen. Psychiatry* 45:577 (1988)]. In addition, there is a blunted adrenocorticotropin (ACTH) response to CRF (i.v. administered) observed in depressed patients [P. W. Gold et al., *Am J. Psychiatry* 141:619 (1984); F. Holsboer et al., *Psychoneuroendocrinology* 9:147 (1984); P. W. Gold et al., *New Eng. J. Med.* 314:1129 (1986)]. Preclinical studies in rats and non-human primates provide additional support for the hypothesis that hypersecretion of CRF may be involved in the symptoms seen in human depression [R. M. Sapolsky, *Arch. Gen. Psychiatry* 46:1047 (1989)]. There is preliminary evidence that tricyclic antidepressants can alter CRF levels and thus modulate the numbers of CRF receptors in brain [Grigoriadis et al., *Neuropsychopharmacology* 2:53 (1989)].

There has also been a role postulated for CRF in the etiology of anxiety-related disorders. CRF produces anxiogenic effects in animals and interactions between benzodiazepine/non-benzodiazepine anxiolytics and CRF have been demonstrated in a variety of behavioral anxiety models [D. R. Britton et al., *Life Sci.* 31:363 (1982); C. W. Berridge and A. J. Dunn Regul. *Peptides* 16:83 (1986)]. Preliminary studies using the putative CRF receptor antagonist a-helical ovine CRF (9–41) in a variety of behavioral paradigms demonstrate that the antagonist produces "anxiolytic-like" effects that are qualitatively similar to the benzodiazepines [C. W. Berridge and A. J. Dunn *Horm. Behav.* 21:393 (1987), *Brain Research Reviews* 15:71 (1990)]. Neurochemical, endocrine and receptor binding studies have all demonstrated interactions between CRF and benzodiazepine anxiolytics providing further evidence for the involvement of CRF in these disorders. Chlordiazepoxide attenuates the "anxiogenic" effects of CRF in both the conflict test [K. T. Britton et al., *Psychopharmacology* 86:170 (1985); K. T. Britton et al., *Psychopharmacology* 94:306 (1988)] and in the acoustic startle test [N. R. Swerdlow et al., *Psychopharmacology* 88:147 (1986)] in rats. The benzodiazepine receptor antagonist (Ro15-1788), which was without behavioral activity alone in the operant conflict test, reversed the effects of CRF in a dose-dependent manner while the benzodiazepine inverse agonist (FG7142) enhanced the actions of CRF [K. T. Britton et al., *Psychopharmacology* 94:306 (1988)].

The mechanisms and sites of action through which the standard anxiolytics and antidepressants produce their therapeutic effects remain to be elucidated. It has been hypothesized however, that they are involved in the suppression of the CRF hypersecretion that is observed in these disorders. Of particular interest is that preliminary studies examining the effects of a CRF receptor antagonist (a-helical $CRF_{9-41}$) in a variety of behavioral paradigms have demonstrated that the CRF antagonist produces "anxiolytic-like" effects qualitatively similar to the benzodiazepines [for review see G. F. Koob and K. T. Britton, In: *Corticotropin-Releasing Factor: Basic and Clinical Studies of a Neuropeptide*, E. B. De Souza and C. B. Nemeroff eds., CRC Press p221 (1990)].

DuPont Merck PCT application US 94/11050 describes corticotropin releasing factor antagonist compounds of the formula:

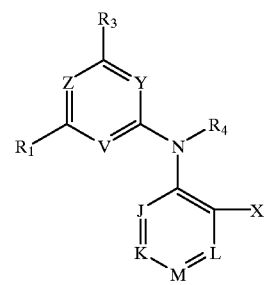

and their use to treat psychiatric disorders and neurological diseases. Included in the description are fused pyridines and pyrimidines of the formula:

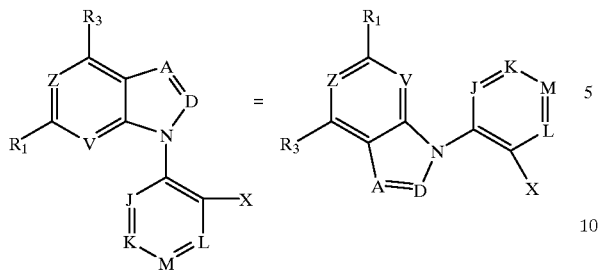

where: Z is $CR^2$ or N; A is $CR^{30}$ or N; D is $CR^{28}$ or N; and $R^3$ can be aryloxy or arylthio.

Pfizer WO 95/33750 describes corticotropin releasing factor antagonist compounds useful in the treatment of CNS and stress disorders. The description includes compounds of the formulae:

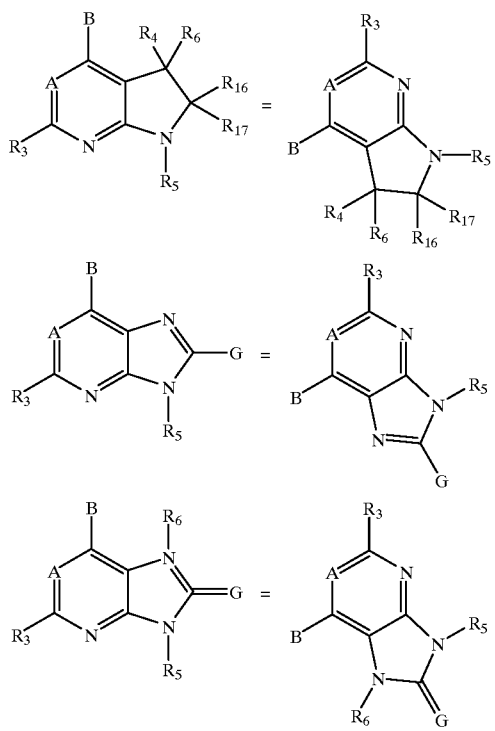

where A is $CR_7$ or N; B is $OCHR_1R_2$ or $SCHR_1R_2$; $R_1$ is substituted or unsubstituted alkyl; $R_2$ is substituted or unsubstituted alkyl, aryl or heteroaryl; $R_3$ is methyl, halo, cyano, methoxy, etc.; $R_4$ is H, substituted or unsubstituted alkyl, halo, amino, nitro, etc.; $R_5$ is substituted or unsubstituted aryl or heteroaryl; $R_6$ is H or substituted or unsubstituted alkyl; $R_7$ is H, methyl, halo, cyano, etc.; $R_{16}$ and $R_{17}$ taken together form an oxo (=O) group; and G is =O, =S, =NH, =NCH$_3$, hydrogen, methyl, methoxy, etc.

Pfizer WO 95/34563 describes corticotropin releasing factor antagonist compounds, including compounds of the formula:

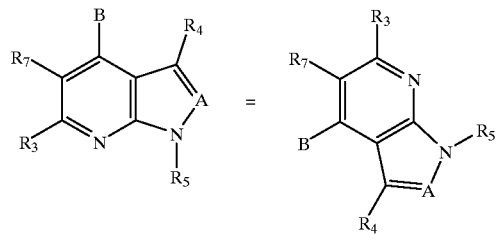

where A, B and the R groups have definitions similar to those in WO 95/33750.

Pfizer WO 95/33727 describes corticotropin releasing factor antagonist compounds of the formula:

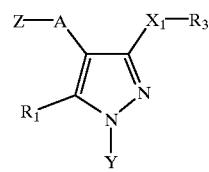

where A is CH$_2$ and Z can be a heteroaryl moiety.

Ganguly et al., U.S. Pat. No. 4,076,711 describes triazolo[4,5-d]pyrimidines of the formula:

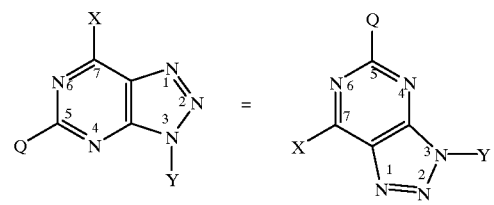

where X is halo, —NR$_1$R or alkoxy, with R1 and R each being H or alkyl; Y is alkyl, cycloalkyl, hydroxycycloalkyl, phenyl, bicycloalkyl or phenylalkyl or bicycloalkylalkyl; and Q is H or Y. The patent states that the compounds are useful in the treatment of psoriasis.

Tanji et al., Chem. Pharm. Bull. 39(11)3037–3040(1991), describes triazolo[4,5-d]pyrimidines of the formula:

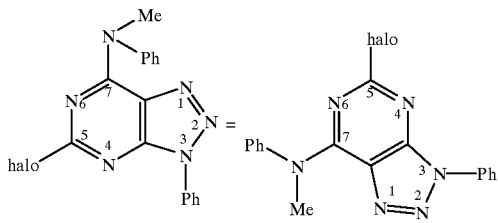

where halo is I, Br or Cl, Ph is phenyl and Me is methyl. No utility for the compounds is described.

Settimo et al., Il Farmaco, Ed. Sc., 35 (4), 308–323 (1980) describes 8-azaadenines (triazolo[4,5-d] pyrimidines) of the formula:

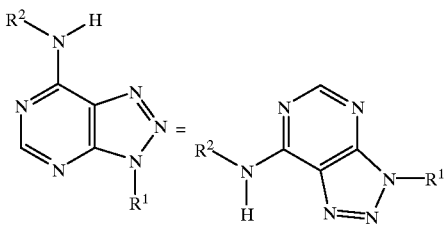

where R1 is H or benzyl and R2 is p-methylphenyl.

Biagi et al., Il Farmaco, 49 (3), 183–186 (1994), describes N(6)-substituted 2-n-butyl-9-benzyl-8-azaadenines of the formula:

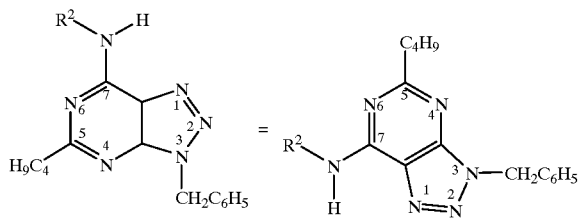

where $R^2$ can be alkyl, phenyl, or benzyl. The paper states that the compounds have affinity for adenosine receptors.

Thompson et al., J. Med. Chem., 1991, 34, 2877–2882, describes $N^6$,9-disubstituted adenines of the formula:

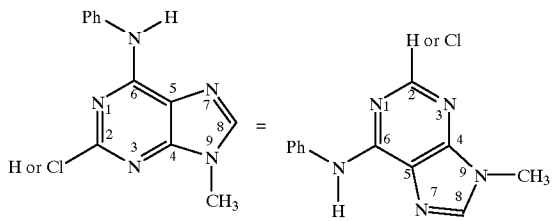

where Ph is phenyl or (when C-2 is unsubstituted) 2-fluorophenyl. The paper states that the compounds have selective affinity for the $A_1$ adenosine receptor.

Kelley et al., J. Med. Chem. 1990, 31, 606–612, describes the compound

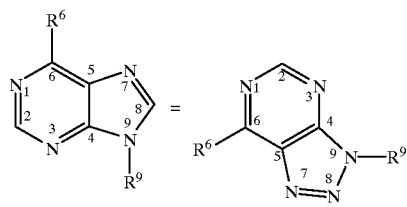

where $R^6$ is $NHC_6H_5$ and $R^9$ is $CH_2C_6H_5$, and reports that the compound was inactive when tested for anticonvulsant activity. The paper reports that various 6-(alkylamino)-9-benzyl-9H-purine analogs of the above compound exhibited anticonvulsant activity.

Kelley et al., J. Med. Chem. 1990, 33, 1360–1363, describes 6-anilino-9-benzyl-2-choro-9H-purines of the formula:

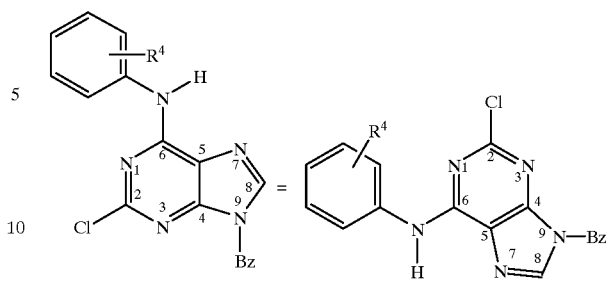

where Bz is benzyl or (when $R^4$ is H) p-methylbenzyl and $R^4$ is H or alkyl, alkoxy, halo, cyano, nitro, etc. Tests of the compounds for antirhinoviral activity are reported.

Kelley et al., J. Heterocyclic Chem., 28, 1099 (1991), describes 6-substituted-9-(3-formamidobenzyl)-9H-purines of the formula:

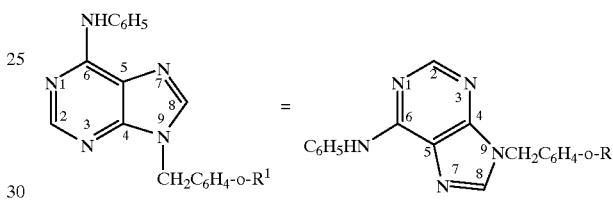

where R1 is NH2 or NHCHO. The compound where R1 is NHCHO was tested for benzodiazepine receptor binding and was inactive, although various analogs were active.

Khairy et al., J. Heterocyclic Chem., 22, 853 (1985), describes synthesis of certain 9-aryl-9H-purin-6-amines of the formula:

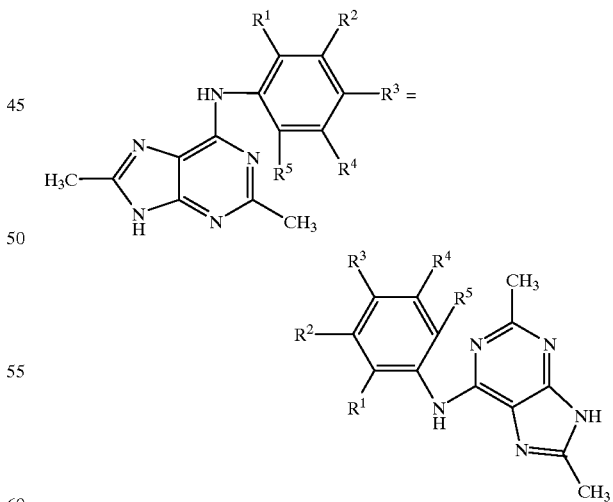

where the R groups are H, methyl, ethyl, isopropyl, chloro or fluoro.

Hoechst EP 298467 (1989) describes azapurine derivatives, including compounds of the structure:

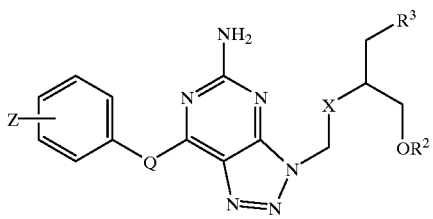

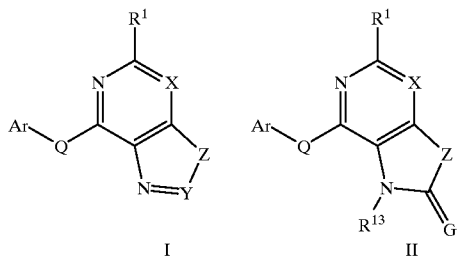

where Q is O, S, SO, $SO_2$ or $NH_2$; X is O, S, SO or $SO_2$; Z is H, halogen, $CF_3$, 1-3C alkoxy or alkylthio; $R^2$ is alkyl or alkoxy; $R^3$ is $OR^2$. These compounds are claimed to be useful for treating virus diseases, autoimmune diseases and cancers.

SS Pharmaceutical Co. Jp 59062595 (1984) and Jp 56131587 (1981) describe triazolopyrimidine derivatives, including compounds of the structure: where Q is O, S, $SO_2$; R is amino or substituted amino, alkoxy, benzyloxy, halogen, or phenylhydrazino. These compounds are claimed to be useful as anticancer agents.

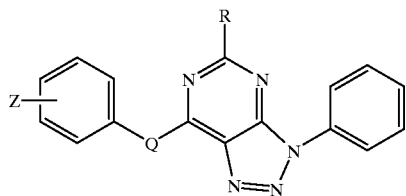

Fuji Jp 60194443 (1985) describe aza-indenes, including compounds of the structure:

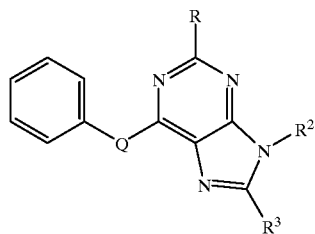

where Q is O, S; $R^1$, $R^2$ and $R^3$ are H, alkyl, aryl, aralkyl, amino, hydroxyl, alkoxy, carbamoyl, aryloxy, alkoxy carbonyl, cyano, halogen, alkylthio, arylthio, carboxyl, or mercapto, provided that at least one of the substituents is mercapto. These compounds are claimed to be useful as light-sensitizing agents, providing high photographic speed and contrast to silver halide emulsions.

SUMMARY OF THE INVENTION

This invention is a class of novel compounds which are CRF receptor antagonists and which can be represented by formula I or formula II:

or a pharmaceutically acceptable salt or pro-drug form thereof, wherein:
X is N or $CR^1$;
Y is N or $CR^2$;
Z is $NR^3$, O, or $S(O)_n$;
G is O or S;
Q is O or S(O)n
Ar is phenyl, naphthyl, pyridyl, pyrimidinyl, triazinyl, furanyl, quinolinyl, isoquinolinyl, thienyl, imidazolyl, thiazolyl, indolyl, pyrrolyl, oxazolyl, benzofuranyl, benzothienyl, benzthiazolyl, isoxazolyl or pyrazolyl, each optionally substituted with 1 to 4 $R^5$ groups;
$R^1$ is independently at each occurrence H, $C_1$–$C_4$ alkyl, $C_2$–$C_4$ alkenyl, $C_2$–$C_4$ alkynyl, halo, CN, $C_1$–$C_4$ haloalkyl, —$NR^9R^{10}$, $NR^9COR^{10}$, —$OR^{11}$, SH or —$S(O)_nR^{12}$;
$R^2$ is H, $C_1$–$C_4$ alkyl, $C_1$–$C_6$ cycloalkyl, halo, CN, —$NR^6R^7$, $NR^9COR^{10}$, $C_1$–$C_4$ haloalkyl, —$OR^7$, SH or —$S(O)_nR^{12}$;
$R^3$ is H, $C_1$–$C_{10}$ alkyl, $C_2$–$C_{10}$ alkenyl, $C_2$–$C_{10}$ alkynyl, $C_3$–$C_8$ cycloalkyl or $C_4$–$C_{12}$ cycloalkylalkyl each optionally substituted with 1 to 3 substituents independently selected at each occurrence from $C_1$–$C_6$ alkyl, $C_3$–$C_6$ cycloalkyl, halo, $C_1$–$C_4$ haloalkyl, cyano, —$OR^7$, SH, —$S(O)_nR_{13}$, —$COR^7$, —$CO_2R^7$, —$OC(O)R^{13}$, —$NR^8COR^7$, —$N(COR^7)_2$, —$NR^8CONR^6R^7$, —$NR^8CO_2R^{13}$, —$NR^6R^7$, —$CONR^6R^7$, aryl, heteroaryl and heterocyclyl, where the aryl, heteroaryl or heterocyclyl is optionally substituted with 1 to 3 substituents independently selected at each occurrence from $C_1$–$C_6$ alkyl, $C_3$–$C_6$ cycloalkyl, halo, $C_1$–$C_4$ haloalkyl, cyano, —$OR^7$, SH, —$S(O)_nR^{13}$, —$COR^7$, —$CO_2R^7$, —$OC(O)R^{13}$, —$NR^8COR^7$, —$N(COR^7)_2$, —$NR^8CONR^6R^7$, —$NR^8CO_2R^{13}$, —$NR^6R^7$, and —$CONR^6R^7$;
$R^5$ is independently at each occurrence $C_1$–$C_{10}$ alkyl, $C_2$–$C_{10}$ alkenyl, $C_2$–$C_{10}$ alkynyl, $C_3$–$C_6$ cycloalkyl, $C_4$–$C_{12}$ cycloalkylalkyl, —$NO_2$, halo, —CN, $C_1$–$C_4$ haloalkyl, —$NR^6R^7$, $NR^8COR^7$, $NR^8CO_2R^7$, —$COR^7$ —$OR^7$, —$CONR^6R^7$, —$CO(NOR^9)R^7$, $CO_2R^7$, or —$S(O)_nR^7$, where $C_1$–$C_{10}$ alkyl, $C_2$–$C_{10}$ alkenyl, $C_2$–$C_{10}$ alkynyl, $C_3$–$C_6$ cycloalkyl and $C_4$—$C_{12}$ cycloalkylalkyl are optionally substituted with 1 to 3 substituents independently selected at each occurrence from $C_1$–$C_4$ alkyl, —$NO_2$, halo, —CN, —$NR^6R^7$, —$NR^6R^7$, $NR^8COR^7$, $NR^8CO_2R^7$, —$COR^7$ —$OR^7$, —$CONR^6R^7$, $CO_2R^7$, —$CO(NOR^9)R^7$, or —$S(O)_nR^7$;
$R^6$ and R7 are independently at each occurrence H, $C_1$–$C_4$ alkyl, $C_1$–$C_4$ haloalkyl, $C_2$–$C_8$ alkoxyalkyl, $C_3$–$C_6$ cycloalkyl, $C_4$–$C_{12}$ cycloalkylalkyl, aryl, aryl($C_1$–$C_4$ alkyl)-, heteroaryl or heteroaryl($C_1$–$C_4$ alkyl)-; or $NR^6R^7$ is piperidine, pyrrolidine, piperazine, N-methylpiperazine, morpholine or thiomorpholine;
$R^8$ is independently at each occurrence H or $C_1$–$C_4$ alkyl;
$R^9$ and $R^{10}$ are independently at each occurrence selected from H, $C_1$–$C_4$ alkyl, or $C_3$–$C_6$ cycloalkyl;

$R^{11}$ is H, $C_1$–$C_4$ alkyl, $C_1$–$C_4$ haloalkyl, or $C_3$–$C_6$ cycloalkyl;

$R^{12}$ is $C_1$–$C_4$ alkyl or $C_1$–$C_4$ haloalkyl;

$R^{13}$ is $C_1$–$C_4$ alkyl, $C_1$–$C_4$ haloalkyl, $C_2$–$C_8$ alkoxyalkyl, $C_3$–$C_6$ cycloalkyl, $C_4$–$C_{12}$ cycloalkylalkyl, aryl, aryl($C_1$–$C_4$ alkyl)-, heteroaryl or heteroaryl($C_1$–$C_4$ alkyl)-;

aryl is phenyl or naphthyl, each optionally substituted with 1 to 3 substituents independently selected at each occurrence from $C_1$–$C_6$ alkyl, $C_3$–$C_6$ cycloalkyl, halo, $C_1$–$C_4$ haloalkyl, cyano, —$OR^7$, SH, —$S(O)_nR^{13}$, —$COR^7$, —$CO_2R^7$, —$OC(O)R^{13}$, —$NR^8COR^7$, —$N(COR^7)_2$, —$NR^8CONR^6R^7$, —$NR^8CO_2R^{13}$, —$NR^6R^7$, and —$CONR^6R^7$;

heteroaryl is pyridyl, pyrimidinyl, triazinyl, furanyl, quinolinyl, isoquinolinyl, thienyl, imidazolyl, thiazolyl, indolyl, pyrrolyl, oxazolyl, benzofuranyl, benzothienyl, benzthiazolyl, isoxazolyl or pyrazolyl optionally substituted with 1 to 3 substituents independently selected at each occurrence from $C_1$–$C_6$ alkyl, $C_3$–$C_6$ cycloalkyl, halo, $C_1$–$C_4$ haloalkyl, cyano, —$OR^7$, SH, —$S(O)_nR^{13}$, —$COR^7$, —$CO_2R^7$, —$OC(O)R^{13}$, —$NR^8COR^7$, —$N(COR^7)_2$, —$NR^8CONR^6R^7$, —$NR^8CO_2R^{13}$, —$NR^6R^7$, and —$CONR^6R^7$;

heterocyclyl is saturated or partially saturated heteroaryl, optionally substituted with 1 to 3 substituents independently selected at each occurrence from $C_1$–$C_6$ alkyl, $C_3$–$C_6$ cycloalkyl, halo, $C_1$–$C_4$ haloalkyl, cyano, —$OR^7$, SH, —$S(O)_nR^{13}$, —$COR^7$, —$CO_2R^7$, —$OC(O)R^{13}$, —$NR^8COR^7$, —$N(COR^7)_2$, —$NR^8CONR^6R^7$, —$NR^8CO_2R^{13}$, —$NR^6R^7$, and —$CONR^6R^7$;

n is independently at each occurrence 0, 1 or 2;

provided that in formula I, when X and Z are each N and Y is $CR^2$, then $R^1$ and $R^2$ cannot be mercapto groups.

Included in this invention is the method of treating affective disorder, anxiety, depression, irritable bowel syndrome, post-traumatic stress disorder, supranuclear palsy, immune suppression, Alzheimer's disease, gastrointestinal disease, anorexia nervosa or other feeding disorder, drug or alcohol withdrawal symptoms, drug addiction, inflammatory disorder, or fertility problem in a mammal comprising administering to the mammal a therapeutically effective amount of a compound of formula I or II.

Also included in this invention are pharmaceutical compositions comprising a pharmaceutically acceptable carrier and a therapeutically effective amount of any one of the above-described compounds.

The compounds provided by this invention (and especially labelled compounds of this invention) are also useful as standards and reagents in determining the ability of a potential pharmaceutical to bind to the CRF receptor.

DETAILED DESCRIPTION OF INVENTION

Many compounds of this invention have one or more asymmetric centers or planes. Unless otherwise indicated, all chiral (enantiomeric and diastereomeric) and racemic forms are included in the present invention. Many geometric isomers of olefins, C=N double bonds, and the like can also be present in the compounds, and all such stable isomers are contemplated in the present invention. The compounds may be isolated in optically active or racemic forms. It is well known in the art how to prepare optically active forms, such as by resolution of racemic forms or by synthesis from optically active starting materials. All chiral, (enantiomeric and diastereomeric) and racemic forms and all geometric isomeric forms of a structure are intended, unless the specific stereochemistry or isomer form is specifically indicated.

The term "alkyl" includes both branched and straight-chain alkyl having the specified number of carbon atoms. "Alkenyl" includes hydrocarbon chains of either a straight or branched configuration and one or more unsaturated carbon-carbon bonds which may occur in any stable point along the chain, such as ethenyl, propenyl, and the like. "Alkynyl" includes hydrocarbon chains of either a straight or branched configuration and one or more triple carbon-carbon bonds which may occur in any stable point along the chain, such as ethynyl, propynyl and the like. "Haloalkyl" is intended to include both branched and straight-chain alkyl having the specified number of carbon atoms, substituted with 1 or more halogen; "alkoxy" represents an alkyl group of indicated number of carbon atoms attached through an oxygen bridge; "cycloalkyl" is intended to include saturated ring groups, including mono-,bi- or poly-cyclic ring systems, such as cyclopropyl, cyclobutyl, cyclopentyl, cyclohexyl, and so forth. "Halo" or "halogen" includes fluoro, chloro, bromo, and iodo.

The term "substituted", as used herein, means that one or more hydrogen on the designated atom is replaced with a selection from the indicated group, provided that the designated atom's normal valency is not exceeded, and that the substitution results in a stable compound. When a substitent is keto (i.e., =O), then 2 hydrogens on the atom are replaced.

Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "pharmaceutically acceptable salts" includes acid or base salts of the compounds of formulas (I) and (II). Examples of pharmaceutically acceptable salts include, but are not limited to, mineral or organic acid salts of basic residues such as amines; alkali or organic salts of acidic residues such as carboxylic acids; and the like.

Pharmaceutically acceptable salts of the compounds of the invention can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

"Prodrugs" are considered to be any covalently bonded carriers which release the active parent drug of formula (I) or (II) in vivo when such prodrug is administered to a mammalian subject. Prodrugs of the compounds of formula (I) and (II) are prepared by modifying functional groups present in the compounds in such a way that the modifications are cleaved, either in routine manipulation or in vivo, to the parent compounds. Prodrugs include compounds wherein hydroxy, amine, or sulfhydryl groups are bonded to any group that, when administered to a mammalian subject, cleaves to form a free hydroxyl, amino, or sulfhydryl group, respectively. Examples of prodrugs include, but are not limited to, acetate, formate and benzoate derivatives of alcohol and amine functional groups in the compounds of formulas (I) and (II); and the like.

The term "therapeutically effective amount" of a compound of this invention means an amount effective to antagonize abnormal level of CRF or treat the symptoms of affective disorder, anxiety or depression in a host.

Synthesis

The novel substituted fused pyrimidines of the present invention are prepared by one of the general schemes outlined below wherein Ar, Q, G, X, Y, Z, $R_1$, $R_2$, $R_3$ and $R_{13}$ are as above and L represents a suitable leaving group such as halo, methanesulfonate, p-toluenesulfonate, or triflate.

4-aminoheptane in solvents such as dioxane at temperatures between 25 and 100° C. These amino adducts are converted into compounds of the type V by reduction with hydrogen in the presence of catalysts such as platinum on carbon at atmospheric or elevated pressure or by reducing agents such as sodium dithionite, or iron in acetic acid.

Compounds of the type VI are prepared from compounds of the type V through diazotization and cyclization with an Scheme 1

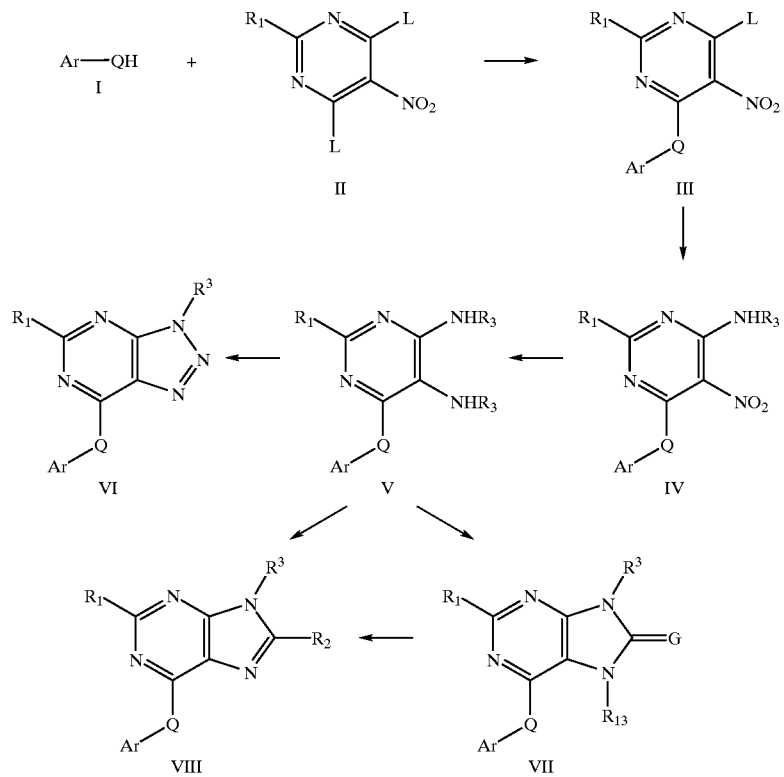

Compounds of the type III (Scheme 1) are prepared by condensing the alkali metal salts of compounds of the type I, where Q=O or S, with compounds of the type II made according to literature procedures [Ashley and Harris, J Chem Soc., 677(1944); Albert et al., J Chem Soc., 3832 (1954)] in solvents such as acetonitrile at temperatures between 0 and 50° C.

Compounds of the type IV are obtained from compounds of the type III by treatment with primary amines such as alkali metal nitrite in the presence of an acid in water with or without an organic cosolvent such as cyclic ethers or aromatic hydrocarbons.

Compounds of type VII are prepared by the condensation of compounds of the type V with phosgene, thiophosgene, carbonyldiimidazole, thiocarbonyldiimidazole, urea, thiourea, guanidine and the like, in the presence or absence of solvents such as high-boiling ethers or aromatic hydrocarbons and at temperatures between 100–200° C.

Scheme 2

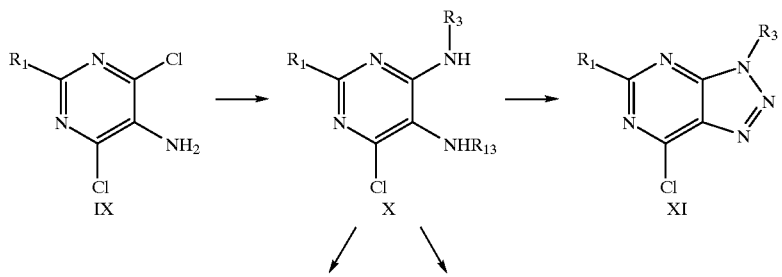

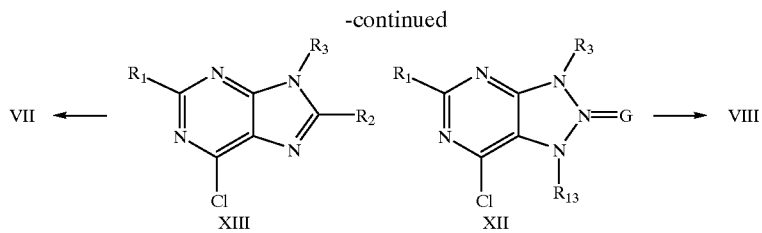

Compounds of the type VIII are prepared by condensation of the compounds of the type V with reagents such as acids, acid chlorides, anhydrides, amides or ortho esters in the presence or absence of solvents such as ethers or aromatic hydrocarbons at temperatures between 0 to 200° C.

Compounds of the type VII, where $R^{13}$=H, are alkylated with reagents such as alkyl halides and the like, in the presence or absence of bases such as sodium hydroxide, in solvents such as tetrahydrofuran or DMF and at temperatures between 0 to 100° C. to yield compounds of the type VIII.

Alternatively, compounds of the type VII are prepared from compounds of the type X (Scheme 2). These diamino pyrimidines, X, are made from the dichloro-aminopyrimidines of type IX which are synthesized from compounds of type II by treatment with reducing agents such as, but not limited to sodium dithionite, iron or zinc in the presence of acid, or catalytic hydrogenation (see: LaRock, Comprehensive Organic Transformations, VCH Publishers, NY, 1989, 411). The diamino compounds, X, are converted into compounds of the type XII using the same procedure as described for the preparation of compounds of the type VII from compounds of the type V, and then condensing compounds of the type XII with salts of the compounds of the type I in solvents such as DMF or 2-ethoxyethanol at temperatures between 25 and 200° C.

Alternatively, compounds of the type VIII are prepared from compounds of the type X by first converting them into compounds of the type XIII using the same method as described for the preparation of compounds of the type VIII from compounds of the type V and then condensing compounds of the type XIII thus obtained with salts of the compounds of the type I under the conditions described for the conversion of compounds of the type I into compounds of the type II.

Alternatively, compounds of type VI are prepared from compounds of type X by diazotization and cyclization, as previously described for compounds of compound type V to compounds of type VI, to give compounds of type XI. Subsequent treatment with the salts of the compounds of the type I with compounds of type XI, as previously described, provides these tiazolo adducts of type VI.

The compounds of the present invention and their synthesis are further illustrated by the following examples and preparations.

EXAMPLE 1

3-Bromo-4-hydroxy-5-methoxyacetophenone

Bromine (9.62 g) in 3 mL of chloroform was added dropwise to a solution of acetovanillone (10.0 g) in 150 mL of chloroform maintained at 0–5° C., such that the temperature did not rise above 5° C. After the addition was complete, the mixture was stirred at 0–5° C. for 4 hours. The residue was treated with water. The organic layer was dried over $MgSO_4$ and stripped of the solvent under reduced pressure to yield a pinkish powder which was tritrated with ether and filtered to yield the title compound, mp 148–152° C.

EXAMPLE 2

3-Bromo-4-hydroxy-5-methoxy-α,α-dimethylbenzenemethanol

Methyl magnesium bromide (3M in diethyl ether, 11.42 mL) was added dropwise to a solution of 5-Bromo-4-hydroxy-3-methoxyacetophenone (3.0 g) in anhydrous tetrahydrofuran (60 mL) maintained at 0–5° C. under $N_2$ gas, such that the temperature did not rise above 5° C. After the addition was complete, the solution was stirred at room temperature for 2 hours. Saturated ammonium chloride was added dropwise until effervescence ceased. The mixture was treated with an excess of saturated ammonium chloride. The organic layer was dried over $MgSO_4$ and stripped of the solvent under reduced pressure to yield the title compound as a viscous oil which solidified over a period of time, mp 107–112° C.

EXAMPLE 3

3-Bromo-5-methoxy-α,α-dimethyl-4-[[6-chloro-2-methyl-5-nitro-4-pyrimidinyl]oxy]benzenemethanol 3-Bromo-4-hydroxy-5-methoxy-α,α-dimethylbenzenemethanol (1.16 g) was dissolved in 10% NaOH (1.78 g) and 5 mL of water. The solvent was stripped under reduced pressure. The salt was taken up in 50 mL acetonitrile and added dropwise by pipette to an already cooled solution (0–5° C.) of 4,6-dichloro-2-methyl-5-nitro-1,3-pyrimidine (0.92 g) in 80 mL of acetonitrile. The mixture was stirred at 0°–5° C. for 3 hours. The solvent was removed under reduced pressure and the residue was extracted with methylene chloride. The extracts were combined and evaporated under reduced pressure to yield the title compound.

EXAMPLE 4

3-Bromo-5-methoxy-α,α-dimethyl-4-[[2-methyl-5-nitro-6-[(1-propylbutyl)amino]-4-pyrimidinyl]oxy]benzenemethanol To a solution of 3-bromo-5-methoxy-α,α-dimethyl-4-[[6-chloro-2-methyl-5-nitro-4-pyrimidinyl]oxy]benzenemethanol (1.88 g) in anhydrous 1,4-dioxane (50 mL) with 0.50 g of potassium carbonate, 4-heptylamine (1.00 mL) was added and the solution was stirred at room temperature for 2 hours. The solvent was removed under reduced pressure and the residue was taken up in water and extracted with methylene chloride. The extracts were combined and dried over $MgSO_4$. The solvent was removed under reduced pressure and the residue was purified by chromatography on silica gel using a 1:1 mixture of ethyl acetate and hexane to yield the title compound, mp 138° C.

3-Bromo-5-methoxy-α,α-dimethyl-4-[(6-(1-methoxypropyl)amino-2-methyl-5-nitro)-4-pyrimidinyl]-oxybenzenemethanol, m.p. 119–120° C., was prepared by the same procedure.

EXAMPLE 5

3-Bromo-5-methoxy-α,α-dimethyl-4-[[5-amino-2-methyl-6-[(1-propylbutyl)amino]-4-pyrimidinyl]oxy] benzenemethanol Platinum black, (5%,0.25 g) was added to a solution of 3-bromo-5-methoxy-α,α-dimethyl-4-[[2-methyl-5-nitro-6-[(1-propyl-butyl)amino]-4-pyrimidinyl]oxy] benzenemethanol (0.80 g) in 50 mL of ethanol. The mixture was hydrogenated at a pressure of 41 psi for 18 hours. The mixture was filtered through celite and the filtrate was stripped under reduced pressure. The residue was taken up in 1N NaOH and extracted with methylene chloride. The combined methylene chloride extracts were dried over $MgSO_4$ and the filtrate was stripped under reduced pressure to yield the title compound, mp 114–116° C.

EXAMPLE 6

3-Bromo-5-methoxy-α,α-dimethyl-4-[(5-methyl-3-(1-propylbutyl)-3H-1,2,3-triazolo[4,5-d]pyrimidin-7-yl)-oxy]benzenemethanol To a solution of 3-bromo-5-methoxy-α,α-dimethyl-4-[[5-amino-2-methyl-6-[(1-propylbutyl)amino]-4-pyrimidinyl] oxy]benzene-methanol (0.70 g) in 35 mL of glacial acetic acid, 0.10 g of sodium nitrite in 1 mL of water was added dropwise. The mixture was stirred at room temperature for 20 minutes and then diluted with water, basified with 1N NaOH and extracted three times with ethyl acetate. The combined extracts were dried over $MgSO_4$ and stripped of the solvent under reduced pressure to yield the title compound as viscous liquid.

EXAMPLE 7

7-[2-Bromo-6-methoxy-4-(1-methylethenyl) phenoxy]-5-methyl-3-(1-propylbutyl)-3H-1,2,3-triazolo[4,5-d]pyrimidine To a solution of 3-bromo-5-methoxy-α,α-dimethyl-4-[(5-methyl-3-(1-propylbutyl)-3H-1,2,3-triazolo[4,5-d] pyrimidin-7-yl)-oxy]benzenemethanol (0.59 g) in 35 mL of benzene, a small quantity of p-toluene sulfonic acid was added. The solution was refluxed under azeotropic conditions for 1.5 hours. Once cooled to room temperature, the solution was washed with saturated $NaHCO_3$ followed by water. The organic phase was dried over $MgSO_4$ and the solvent was removed under reduced pressure. The residue was chromatographed silica gel using a mixture of 1:1 ethyl acetate and hexane to yield the title compound as a colorless solid, mp 110–115° C.

EXAMPLE 8

7-[2-Bromo-6-methoxy-4-(1-methylethyl)phenoxy]-5-methyl-3-(1-propylbutyl)-3H-1,2,3-triazolo[4,5-d] pyrimidine Platinum black, 5% (0.19 g) was added to a solution of 7-[2-bromo-6-methoxy-4-(1-methylethenyl)phenoxy]-5-methyl-3-(1-propylbutyl)-3H-1,2,3-triazolo[4,5-d] pyrimidine (0.17 g) in 50 mL of ethanol. The mixture was hydrogenated at a pressure of 40 psi for 18 hours and filtered through celite. The filtrate was stripped of the solvent under reduced pressure and the residue recrystallized from hexane to yield the title compound as a colorless crystalline solid, mp 129–131° C.

EXAMPLE 9

3-(1-Ethylpropyl)-5-methyl-7-(2,4,6-trimethylphenoxy)-3H-1,2,3-triazolo[4,5-d] pyrimidine 2,4,6-Trimethylphenol (0.114) was added to a solution of sodium methoxide (0.334 g) methanol (10 mL) and the resulting solution was evaporated to dryness under reduced pressure. The salt thus obtained was taken up in 10 mL of acetonitrile and added dropwise by to a cold solution (0–5° C.) of 7-chloro-3-(1-ethylpropyl)-5-methyl-3H-1,2,3-triazolo[4,5-d]pyrimidine in 35 mL of acetonitrile, such that the temperature did not rise above 5° C. The mixture was stirred at 0–5° C. for 3 hours. The solvent was then removed from the mixture under reduced pressure and the residue treated with water and extracted three times with methylene chloride. The combined extracts were dried over $MgSO_4$ and stripped of the solvent under reduced pressure. The material was purified on silica gel using a solution of 1% methanol in methylene chloride to yield the title compound as a colorless powder, mp 92° C.

EXAMPLE 10

6-(1-Methoxypropyl)amino-2-methyl-5-nitro-4-[(2-bromo-6-methoxy-4-(1-methylethenyl)phenoxy]-pyrimidine A few crystals of 4-toluenesulfonic acid were added to a solution of 3-bromo-5-methoxy-a,a-dimethyl-4-[[6-(1-methoxypropyl)amino-2-methyl-5-nitro]-pyrimidinyl]]oxy-benzenemethanol (1.70 g) in benzene (30 ml) and the resulting mixture was heated overnight under reflux using Dean-Stark trap. It was then cooled diluted with benzene (70 mL), washed sucessively with 1N aq. NaOH and water, dried over magnesium sulfate and evaporated to dryness underreduced pressure to yield a semi solid which upon trituration with ether and filtration yielded a yellow solid. Recrystallization from ethanol furnished the title compound as a light yellow crystalline solid, m.p. 136–137° C.

EXAMPLE 11

2-Amino-6-(1-methoxypropyl)amino-2-methyl-4-[(2-bromo-6-methoxy-4-(1-methylethyl)phenoxy] pyrimidine Platinum black (5%, 250 mg) was added carefully to a solution of 6-(1-methoxypropyl)amino-2-methyl-5-nitro-4-[(2-bromo-6-methoxy-4(1-methylethenyl)phenoxy] pyrimidine (550 mg) in ethyl acetate (100 mL) and the resulting mixture was hydrogenated at 30 p.s.i. overnight. The mixture was then filtered through a pad of celite and the filtrate evaporated to dryness under reduced pressure to yield the title com-pound as a highly viscous liquid.

EXAMPLE 12

7-[2-Bromo-6-methoxy-3-(1-methoxypropyl)-5-methyl-4-(1-methylethyl)phenoxy]-3H-1,2,3-triazolo [4,5-d]pyrimidine A solution of of sodium nitrite (42 mg) in water (1 mL) was added dropwise to a solution of 2-amino-6-(1- methoxypropyl)-amino-2-methyl-4-[(2-bromo-6-methoxy-4-(1-methylethyl)-phenoxy]pyrimidine (270 mg) in acetic acid (10 mL) with stirring at room temperature. After the addititon was complete, the mixture was stirred overnight at room temperature over night and stripped of most of the acetic acid under reduced pressure. The residue was treated with 1N aq. NaOH and extracted with ethyl acetate (2×). The ethyl acetate extract was was washed with water, dried over magnesium sulfate and evaporated to dryness under reduced pressure to yield a semi-solid which was chromatographed over silica using 1:1 ethyl acetate:hexane as the eluent to furnish the title compound, m.p. 149–150° C.

Utility

CRF-R1 Receptor Binding Assay for the Evaluation of Biological Activity

The following is a description of the isolation of cell membranes containing cloned human CRF-R1 receptors for use in the standard binding assay as well as a description of the assay itself.

Messenger RNA was isolated from human hippocampus. The mRNA was reverse transcribed using oligo (dt) 12–18 and the coding region was amplified by PCR from start to stop codons The resulting PCR fragment was cloned into the EcoRV site of pGEMV, from whence the insert was reclaimed using XhoI+XbaI and cloned into the XhoI+XbaI sites of vector pm3ar (which contains a CMV promoter, the SV40 't' splice and early poly A signals, an Epstein-Barr viral origin of replication, and a hygromycin selectable marker). The resulting expression vector, called phchCRFR was transfected in 293EBNA cells and cells retaining the episome were selected in the presence of 400 $\mu$M hygromycin. Cells surviving 4 weeks of selection in hygromycin were pooled, adapted to growth in suspension and used to generate membranes for the binding assay described below. Individual aliquots containing approximately $1 \times 10^8$ of the suspended cells were then centrifuged to form a pellet and frozen.

For the binding assay a frozen pellet described above containing 293EBNA cells transfected with hCRFR1 receptors is homogenized in 10 ml of ice cold tissue buffer (50 mM HEPES buffer pH 7.0, containing 10 mM $MgCl_2$, 2 mM EGTA, 1 $\mu$g/l aprotinin, 1 $\mu$g/ml leupeptin and 1 $\mu$g/ml pepstatin). The homogenate is centrifuged at 40,000×g for 12 min and the resulting pellet rehomogenized in 10 ml of tissue buffer. After another centrifugation at 40,000×g for 12 min, the pellet is resuspended to a protein concentration of 360 $\mu$g/ml to be used in the assay.

Binding assays are performed in 96 well plates; each well having a 300 $\mu$l capacity. To each well is added 50 $\mu$l of test drug dilutions (final concentration of drugs range from $10^{-10}$–$10^{-5}$ M), 100 $\mu$l of $^{125}$I-ovine-CRF ($^{125}$I-o-CRF) (final concentration 150 pM) and 150 $\mu$l of the cell homogenate described above. Plates are then allowed to incubate at room temperature for 2 hours before filtering the incubate over GF/F filters (presoaked with 0.3% polyethyleneimine) using an appropriate cell harvester. Filters are rinsed 2 times with ice cold assay buffer before removing individual filters and assessing them for radioactivity on a gamma counter.

Curves of the inhibition of $^{125}$I-o-CRF binding to cell membranes at various dilutions of test drug are analyzed by the iterative curve fitting program LIGAND [P. J. Munson and D. Rodbard, *Anal. Biochem.* 107:220 (1980), which provides Ki values for inhibition which are then used to assess biological activity.

A compound is considered to be active if it has a $K_i$ value of less than about 10000 nM for the inhibition of CRF to its receptor.

Inhibition of CRF-Stimulated Adenylate Cyclase Activity

Inhibition of CRF-stimulated adenylate cyclase activity was performed as described by G. Battaglia et al. *Synapse* 1:572 (1987). Briefly, assays were carried out at 37° C. for 10 min in 200 ml of buffer containing 100 mM Tris-HCl (pH 7.4 at 37° C.), 10 mM $MgCl_2$, 0.4 mM EGTA, 0.1% BSA, 1 mM isobutylmethylxanthine (IBMX), 250 units/ml phosphocreatine kinase, 5 mM creatine phosphate, 100 mM guanosine 5'-triphosphate, 100 nM oCRF, antagonist peptides (concentration range $10^{-9}$ to $10^{-6m}$) and 0.8 mg original wet weight tissue (approximately 40–60 mg protein). Reactions were initiated by the addition of 1 mM ATP/$^{32}$P] ATP (approximately 2–4 mCi/tube) and terminated by the addition of 100 ml of 50 mM Tris-HCL, 45 mM ATP and 2% sodium dodecyl sulfate. In order to monitor the recovery of cAMP, 1 $\mu$l of [$^3$H]cAMP (approximately 40,000 dpm) was added to each tube prior to separation. The separation of [$^{32}$P]cAMP from [$^{32}$P]ATP was performed by sequential elution over Dowex and alumina columns. Recovery was consistently greater than 80%.

Some compounds of this invention were tested in this assay and found to be active.

In vivo Biological Assay

The in vivo activity of the compounds of the present invention can be assessed using any one of the biological assays available and accepted within the art. Illustrative of these tests include the Acoustic Startle Assay, the Stair Climbing Test, and the Chronic Administration Assay. These and other models useful for the testing of compounds of the present invention have been outlined in C. W. Berridge and A. J. Dunn *Brain Research Reviews* 15:71 (1990)

Compounds may be tested in any species of rodent or small mammal. Disclosure of the assays herein is not intended to limit the enablement of the invention.

The compounds of this invention have utility in the treatment of inbalances associated with abnormal levels of corticotropin releasing factor in patients suffering from depression, affective disorders, and/or anxiety.

Compounds of this invention can be administered to treat these abnormalities by means that produce contact of the active agent with the agent's site of action in the body of a mammal. The compounds can be administered by any conventional means available for use in conjunction with pharmaceuticals either as individual therapeutic agent or in combination of therapeutic agents. They can be administered alone, but will generally be administered with a pharmaceutical carrier selected on the basis of the chosen route of administration and standard pharmaceutical practice.

The dosage administered will vary depending on the use and known factors such as pharmacodynamic character of the particular agent, and its mode and route of administration; the recipient's age, weight, and health; nature and extent of symptoms; kind of concurrent treatment; frequency of treatment; and desired effect. For use in the treatment of said diseases or conditions, the compounds of this invention can be orally administered daily at a dosage of the active ingredient of 0.002 to 200 mg/kg of body weight. Ordinarily, a dose of 0.01 to 10 mg/kg in divided doses one to four times a day, or in sustained release formulation will be effective in obtaining the desired pharmacological effect.

Dosage forms (compositions) suitable for administration contain from about 1 mg to about 100 mg of active ingredient per unit. In these pharmaceutical compositions, the active ingredient will ordinarily be present in an amount of about 0.5 to 95% by weight based on the total weight of the composition.

The active ingredient can be administered orally is solid dosage forms, such as capsules, tablets and powders; or in liquid forms such as elixirs, syrups, and/or suspensions. The compounds of this invention can also be administered parenterally in sterile liquid dose formulations.

Gelatin capsules can be used to contain the active ingredient and a suitable carrier such as but not limited to lactose, starch, magnesium stearate, steric acid, or cellulose derivatives. Similar diluents can be used to make compressed tablets. Both tablets and capsules can be manufactured as sustained release products to provide for continuous release of medication over a period of time. Compressed tablets can be sugar-coated or film-coated to mask any unpleasant taste, or used to protect the active ingredients from the atmosphere, or to allow selective disintegration of the tablet in the gastrointestinal tract.

Liquid dose forms for oral administration can contain coloring or flavoring agents to increase patient acceptance.

In general, water, pharmaceutically acceptable oils, saline, aqueous dextrose (glucose), and related sugar solutions and glycols, such as propylene glycol or polyethylene glycol, are suitable carriers for parenteral solutions. Solutions for parenteral administration preferably contain a water soluble salt of the active ingredient, suitable stabilizing agents, and if necessary, butter substances. Antioxidizing agents, such as sodium bisulfite, sodium sulfite, or ascorbic acid, either alone or in combination, are suitable stabilizing agents. Also used are citric acid and its salts, and EDTA. In addition, parenteral solutions can contain preservatives such as benzalkonium chloride, methyl- or propyl-paraben, and chlorobutanol.

Suitable pharmaceutical carriers are described in "Remington's Pharmaceutical Sciences", A. Osol, a standard reference in the field.

Useful pharmaceutical dosage-forms for administration of the compounds of this invention can be illustrated as follows:

Capsules

A large number of units capsules are prepared by filling standard two-piece hard gelatin capsules each with 100 mg of powdered active ingredient, 150 mg lactose, 50 mg cellulose, and 6 mg magnesium stearate.

Soft Gelatin Capsules

A mixture of active ingredient in a digestible oil such as soybean, cottonseed oil, or olive oil is prepared and injected by means of a positive displacement was pumped into gelatin to form soft gelatin capsules containing 100 mg of the active ingredient. The capsules were washed and dried.

Tablets

A large number of tablets are prepared by conventional procedures so that the dosage unit was 100 mg active ingredient, 0.2 mg of colloidal silicon dioxide, 5 mg of magnesium stearate, 275 mg of microcrystalline cellulose, 11 mg of starch, and 98.8 mg lactose. Appropriate coatings may be applied to increase palatability or delayed adsorption.

The compounds of this invention may also be used as reagents or standards in the biochemical study of neurological function, dysfunction, and disease.

What is claimed is:
1. A compound of formula I:

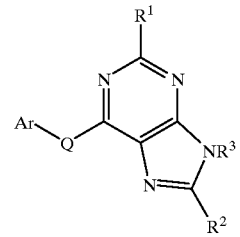

or a pharmaceutically acceptable salt thereof, wherein:
Q is O or S(O)n;
Ar is phenyl, naphthyl, pyridyl, pyrimidinyl, triazinyl, furanyl, quinolinyl, isoquinolinyl, thienyl, imidazolyl, thiazolyl, indolyl, pyrrolyl, oxazolyl, benzofuranyl, benzothienyl, benzthiazolyl, isoxazolyl or pyrazolyl, each optionally substituted with 1 to 4 $R^5$ groups;
$R^1$ is independently at each occurrence H, $C_1$–$C_4$ alkyl, $C_2$–$C_4$ alkenyl, $C_2$–$C_4$ alkynyl, halo, CN, $C_1$–$C_4$ haloalkyl, —$NR^9R^{10}$, $NR^9COR^{10}$, —$OR^{11}$, SH or —$S(O)_nR^{12}$;
$R^2$ is $C_1$–$C_4$ alkyl, $C_1$–$C_6$ cycloalkyl, halo, CN, —$NR^6R^7$, $NR^9COR^{10}$, $C_1$–$C_4$ haloalkyl, —$OR^7$, SH or —$S(O)_nR^{12}$;
$R^3$ is $C_1$–$C_{10}$ alkyl, $C_2$–$C_{10}$ alkenyl, $C_2$–$C_{10}$alkynyl, $C_3$–$C_8$ cycloalkyl or $C_4$–$C_{12}$ cycloalkylalkyl each optionally substituted with 1 to 3 substituents independently selected at each occurrence from $C_1$–$C_6$ alkyl, $C_3$–$C_6$ cycloalkyl, halo, $C_1$–$C_4$ haloalkyl, cyano, —$OR^7$, SH, —$S(O)_nR^{13}$, —$COR^7$, —$CO_2R^7$, —$OC(O)R^{13}$, —$NR^8COR^7$, —$N(COR^7)_2$, —$NR^8CONR^6R^7$, —$NR^8CO_2R^{13}$, —$NR^6R^7$, —$CONR^6R^7$, heteroaryl and heterocyclyl, where the heteroaryl or heterocyclyl is optionally substituted with 1 to 3 substituents independently selected at each occurrence from $C_1$–$C_6$ alkyl, $C_3$–$C_6$ cycloalkyl, halo, $C_1$–$C_4$ haloalkyl, cyano, —$OR^7$, SH, —$S(O)_nR^{13}$, —$COR^7$, —$CO_2R^7$, —$OC(O)R^{13}$, —$NR^8COR^7$, —$N(COR^7)_2$, —$NR^8CONR^6R^7$, —$NR^8CO_2R^{13}$, —$NR^6R^7$, and —$CONR^6R^7$;
$R^5$ is independently at each occurrence $C_1$–$C_{10}$ alkyl, $C_2$–$C_{10}$ alkenyl, $C_2$–$C_{10}$ alkynyl, $C_3$–$C_6$ cycloalkyl, $C_4$–$C_{12}$ cycloalkylalkyl, —$NO_2$, halo, —CN, $C_1$–$C_4$ haloalkyl, —$NR^6R^7$, $NR^8COR^7$, $NR^8CO_2R^7$, —$COR^7$ —$OR^7$, —$CONR^6R^7$, —$CO(NOR^9)R^7$, $CO_2R^7$, or —$S(O)_nR^7$, where $C_1$–$C_{10}$ alkyl, $C_2$–$C_{10}$ alkenyl, $C_2$–$C_{10}$ alkynyl, $C_3$–$C_6$ cycloalkyl and $C_4$–$C_{12}$ cycloalkylalkyl are optionally substituted with 1 to 3 substituents independently selected at each occurrence from $C_1$–$C_4$ alkyl, —$NO_2$, halo, —CN, —$NR^6R^7$, —$NR^6R^7$, $NR^8COR^7$, $NR^8CO_2R^7$, —$COR^7$ —$OR^7$, —$CONR^6R^7$, $CO_2R^7$, —$CO(NOR^9)R^7$, or —$S(O)_nR^7$;
$R^6$ and $R^7$ are independently at each occurrence H, $C_1$–$C_4$ alkyl, $C_1$–$C_4$ haloalkyl, $C_2$–$C_8$ alkoxyalkyl, $C_3$–$C_6$ cycloalkyl, $C_4$–$C_{12}$ cycloalkylalkyl, aryl, aryl($C_1$–$C_4$ alkyl)-, heteroaryl or heteroaryl($C_1$–$C_4$ alkyl)-; or $NR^6R^7$ is piperidine, pyrrolidine, piperazine, N-methylpiperazine, morpholine or thiomorpholine;
$R^8$ is independently at each occurrence H or $C_1$–$C_4$ alkyl;
$R^9$ and $R^{10}$ are independently at each occurrence selected from H, $C_1$–$C_4$ alkyl, or $C_3$–$C_6$ cycloalkyl;
$R^{11}$ is H, $C_1$–$C_4$ alkyl, $C_1$–$C_4$ haloalkyl, or $C_3$–$C_6$ cycloalkyl;

$R^{12}$ is $C_1$–$C_4$ alkyl or $C_1$–$C_4$ haloalkyl;

$R^{13}$ is $C_1$–$C_4$ alkyl, $C_1$–$C_4$ haloalkyl, $C_2$–$C_8$ alkoxyalkyl, $C_3$–$C_6$ cycloalkyl or $C_4$–$C_{12}$cycloalkylalkyl, aryl, aryl($C_1$–$C_4$ alkyl)-, heteroaryl or heteroaryl($C_1$–$C_4$ alkyl)-;

$R^{13a}$ is $C_1$–$C_4$ alkyl, $C_1$–$C_4$ haloalkyl, $C_2$–$C_8$ alkoxyalkyl, $C_3$–$C_6$ cycloalkyl or $C_4$–$C_{12}$ cycloalkylalkyl;

aryl is phenyl or naphthyl, each optionally substituted with 1 to 3 substituents independently selected at each occurrence from $C_1$–$C_6$ alkyl, $C_3$–$C_6$ cycloalkyl, halo, $C_1$–$C_4$ haloalkyl, cyano, —$OR^7$, SH, —$S(O)_nR^{13a}$, —$COR^7$, —$CO_2R^7$, —$OC(O)R^{13a}$, —$NR^8COR^7$, —$N(COR^7)_2$, —$NR^8CONR^6R^7$, $NR^8CO_2R^{13a}$, —$NR^6R^7$, and —$CONR^6R^7$;

heteroaryl is pyridyl, pyrimidinyl, triazinyl, furanyl, quinolinyl, isoquinolinyl, thienyl, imidazolyl, thiazolyl, indolyl, pyrrolyl, oxazolyl, benzofuranyl, benzothienyl, benzthiazolyl, isoxazolyl or pyrazolyl optionally substituted with 1 to 3 substituents independently selected at each occurrence from $C_1$–$C_6$ alkyl, $C_3$–$C_6$ cycloalkyl, halo, $C_1$–$C_4$ haloalkyl, cyano, —$OR^7$, SH, —$S(O)_nR^{13a}$, —$COR^7$, —$CO_2R^7$, —$OC(O)R^{13a}$, —$NR^8COR^7$, —$N(COR^7)_2$, —$NR^8CONR^6R^7$, —$NR^8CO_2R^{13a}$, —$NR^6R^7$, and —$CONR^6R^7$;

heterocyclyl is saturated or partially saturated heteroaryl, optionally substituted with 1 to 3 substituents independently selected at each occurrence from $C_1$–$C_6$ alkyl, $C_3$–$C_6$ cycloalkyl, halo, $C_1$–$C_4$ haloalkyl, cyano, —$OR^7$, SH, —$S(O)_nR^{13a}$, —$COR^7$, —$CO_2R^7$, —$OC(O)R^{13a}$, —$NR^8COR^7$, —$N(COR^7)_2$, —$NR^8CONR^6R^7$, —$NR^8CO_2R^{13a}$, —$NR^6R^7$, and —$CONR^6R^7$; and, n is independently at each occurrence 0, 1 or 2.

2. The compound of claim 1, wherein aryl is phenyl substituted with 1 to 3 substituents independently selected at each occurrence from $C_1$–$C_6$ alkyl, $C_3$–$C_6$ cycloalkyl, halo, $C_1$–$C_4$ haloalkyl, cyano, —$OR^7$, SH, —$S(O)_nR^{13a}$, —$COR^7$, —$CO_2R^7$, —$OC(O)R^{13a}$, —$NR^8COR^7$, —$N(COR^7)_2$, —$NR^8CONR^6R^7$, —$NR^8CO_2R^{13a}$, —$NR^6R^7$, and —$CONR^6R^7$.

3. The compound of claim 2, wherein aryl is phenyl substituted with 1 to 3 substituents independently selected at each occurrence from $C_1$–$C_6$ alkyl, halo, and —$COR^7$.

4. A pharmaceutical composition comprising a therapeutically effective amount of the compound of claim 1 and a pharmaceutically acceptable carrier.

5. A method of treating anxiety or depression in a mammal which comprises administering to the mammal the pharmaceutical composition of claim 4.

* * * * *